United States Patent [19]
Zamierowski

[11] Patent Number: 6,071,267
[45] Date of Patent: Jun. 6, 2000

[54] MEDICAL PATIENT FLUID MANAGEMENT INTERFACE SYSTEM AND METHOD

[75] Inventor: David S. Zamierowski, Shawnee Mission, Kans.

[73] Assignee: Kinetic Concepts, Inc., San Antonio, Tex.

[21] Appl. No.: 09/019,419

[22] Filed: Feb. 6, 1998

[51] Int. Cl.$^7$ .................................................. A61M 35/00
[52] U.S. Cl. ........................... 604/289; 604/305; 604/308
[58] Field of Search ..................................... 604/289, 304, 604/305, 307, 308, 312, 313, 180, 181, 183; 602/42, 43, 47, 48, 52, 54, 56, 57, 58; 424/447, 448, 449

[56] References Cited

U.S. PATENT DOCUMENTS

| | | |
|---|---|---|
| 1,355,846 | 10/1920 | Rannells . |
| 2,547,758 | 4/1951 | Keeling . |
| 2,632,443 | 3/1953 | Lesher . |
| 2,682,873 | 7/1954 | Evans et al. . |
| 2,969,057 | 1/1961 | Simmons . |
| 3,367,332 | 2/1968 | Groves . |
| 3,648,692 | 3/1972 | Wheeler . |
| 3,682,180 | 8/1972 | McFarlane . |
| 3,826,254 | 7/1974 | Mellor . |
| 4,080,970 | 3/1978 | Miller . |
| 4,096,853 | 6/1978 | Weigand . |
| 4,139,004 | 2/1979 | Gonzalez . |
| 4,165,748 | 8/1979 | Johnson . |
| 4,245,630 | 1/1981 | Lloyd et al. . |
| 4,261,363 | 4/1981 | Russo . |
| 4,275,721 | 6/1981 | Olson . |
| 4,297,995 | 11/1981 | Golub . |
| 4,333,468 | 6/1982 | Geist . |
| 4,373,519 | 2/1983 | Errede et al. . |
| 4,382,441 | 5/1983 | Svedman . |
| 4,392,853 | 7/1983 | Muto . |
| 4,392,858 | 7/1983 | George et al. . |
| 4,419,097 | 12/1983 | Rowland . |
| 4,475,909 | 10/1984 | Eisenberg . |
| 4,480,638 | 11/1984 | Schmid . |
| 4,525,166 | 6/1985 | Leclerc . |
| 4,525,374 | 6/1985 | Vailancourt . |
| 4,540,412 | 9/1985 | Van Overloop . |
| 4,543,100 | 9/1985 | Brodsky . |
| 4,551,139 | 11/1985 | Plaas et al. . |
| 4,569,348 | 2/1986 | Hasslinger . |
| 4,605,399 | 8/1986 | Weston et al. . |
| 4,608,041 | 8/1986 | Nielson . |
| 4,640,688 | 2/1987 | Hauser . |
| 4,655,754 | 4/1987 | Richmond et al. . |
| 4,733,659 | 3/1988 | Edenbank et al. . |
| 4,743,232 | 5/1988 | Kruger . |
| 4,787,888 | 11/1988 | Fox .......................................... 604/304 |
| 4,826,949 | 5/1989 | Richmond et al. . |
| 4,838,883 | 6/1989 | Matsuura . |
| 4,840,187 | 6/1989 | Brazier . |
| 4,863,449 | 9/1989 | Therriault et al. . |
| 4,872,450 | 10/1989 | Austad . |
| 4,878,901 | 11/1989 | Sachse . |
| 4,897,081 | 1/1990 | Poirier et al. . |
| 4,906,233 | 3/1990 | Moriuchi et al. . |
| 4,906,240 | 3/1990 | Reed et al. . |
| 4,919,654 | 4/1990 | Kait . |
| 4,941,882 | 7/1990 | Ward et al. . |
| 4,953,565 | 9/1990 | Tachibana et al. . |

(List continued on next page.)

Primary Examiner—Corrine McDermott
Assistant Examiner—David J. Cho
Attorney, Agent, or Firm—Litman, Kraai & Brown LLC; Mark E. Brown

[57] ABSTRACT

A patient interface system includes a fluid transfer subsystem comprising a primary fluid transfer element fluidically communicating with the wound and a secondary fluid transfer element/manifold in contact therewith. A drape subsystem covers the fluid transfer elements and includes a film material membrane. A fluid conveying subsystem includes a vacuum source connected to the secondary fluid transfer element/manifold by a suction tube for creating a negative, sub-atmospheric pressure within the interface system for extracting fluids collected in the interface system. A fluid supply is provided for supplying various types of fluids to the interface system.

22 Claims, 7 Drawing Sheets

U.S. PATENT DOCUMENTS

| | | |
|---|---|---|
| 4,969,880 | 11/1990 | Zamierowski . |
| 4,985,019 | 1/1991 | Michelson . |
| 5,037,397 | 8/1991 | Kalt et al. . |
| 5,100,396 | 3/1992 | Zamierowski . |
| 5,149,331 | 9/1992 | Ferdman et al. . |
| 5,167,613 | 12/1992 | Karami et al. ............................ 604/42 |
| 5,176,663 | 1/1993 | Svedman et al. ....................... 604/305 |
| 5,261,893 | 11/1993 | Zamierwoski . |
| 5,298,015 | 3/1994 | Komatsuzaki et al. . |
| 5,344,415 | 9/1994 | Debusk et al. .......................... 604/304 |
| 5,358,494 | 10/1994 | Svedman ................................. 604/313 |
| 5,556,375 | 9/1996 | Ewall ....................................... 602/43 |
| 5,607,388 | 3/1997 | Ewall ....................................... 602/92 |
| 5,636,643 | 6/1997 | Argenta et al. . |
| 5,645,081 | 7/1997 | Argenta et al. .- |

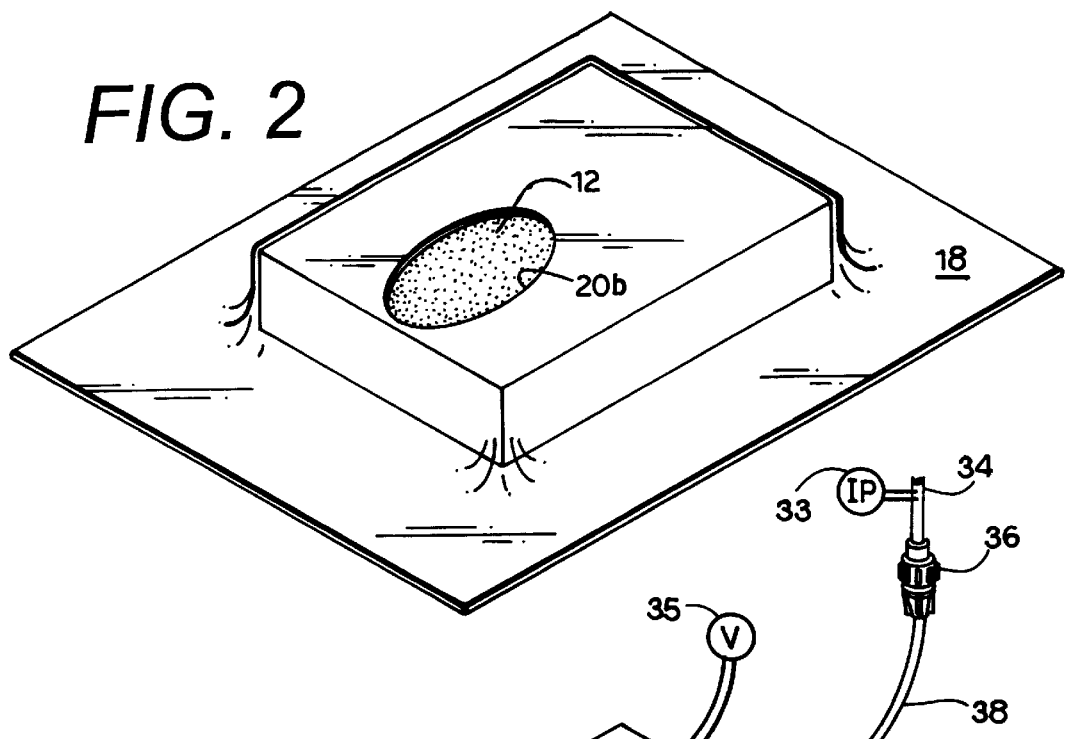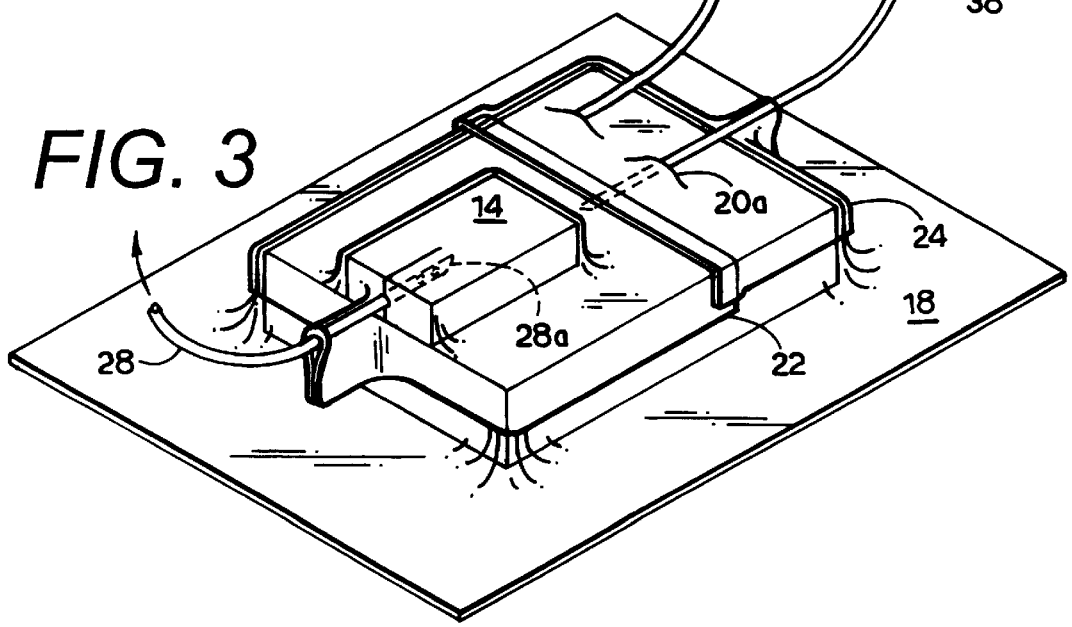

MEDICAL PATIENT FLUID MANAGEMENT INTERFACE SYSTEM AND METHOD

CROSS-REFERENCED TO RELATED DISCLOSURE DOCUMENTS

This application relates to Disclosure Document Nos. 414,622 for VAC® System Applications; Wound Dressings, filed Feb. 18, 1997; and No. 415,021 for Concepts For Use of Biodegradable Beads and Vacuum Bag In VAC® System Applications; Wound Dressings, filed Feb. 28, 1997, which are incorporated herein by reference.

BACKGROUND OF THE INVENTION

I. Field of the Invention

The present invention relates generally to patient interfaces for fluid management in medical care, and in particular to a system for interfacing a vacuum-assisted fluid extraction/supply system with a patient.

II. Description of Related Art

Fluid management significantly affects many aspects of health care and is involved in many medical procedures. For example, wound care typically involves absorbing and/or draining blood, serum and other body fluids from the patient. Various surgical procedures also require fluid drainage. For example, skin grafts have fluid drainage that needs to be managed at both the donor and graft sites.

Various types of porous, absorbent dressing materials have been used for dressing wounds to accumulate body fluids. The dressing materials facilitate drainage and also collection and disposal of the fluids. A disadvantage with many conventional dressings is that they require changing to reduce risks of infection and to maintain effectiveness. However, dressing changes can add significantly to treatment costs and are associated with patient discomfort and medical risks such as infection and damage to reepithelialized tissue. Accordingly, vacuum sources have been employed to drain wounds. For example, Zamierowski U.S. Pat. No. 4,969,880; U.S. Pat. No. 5,100,396; U.S. Pat. No. 5,261,893; and U.S. Pat. No. 5,527,293 pertain to wound dressings, fluid connections, fastening systems and medical procedures utilizing same in connection with vacuum-assisted wound drainage, and are incorporated herein by reference.

A wound drainage device using a hand-operated suction bulb is shown in the George, et al. U.S. Pat. No. 4,392,858. Motorized suction pumps can be employed to provide consistent, sub-atmospheric vacuum pressure for maintaining an effective drainage flow. The Richmond et al. U.S. Pat. No. 4,655,754 and U.S. Pat. No. 4,826,494 disclose vacuum wound drainage systems which can be connected to motorized vacuum pumps.

Another important objective in designing an effective wound drainage system is to provide an effective interface with the patient. Ideally the patient interface should accommodate various types of wounds in different stages of recovery for as broad a range of applications as possible. Promoting optimum wound healing typically involves maintaining the right moisture level to avoid overdrying without causing the wound to macerate from excessive moisture. Pressures should be sufficient for effective drainage without creating significant negative forces, which could cause pressure necrosis or separate freshly-applied skin grafts.

Wound treatment procedures can also include infusing wound sites with liquids to flush contaminants, counter infection, promote healing growth and anesthetize the wound. Prior art fluid delivery systems include a device for treating tissues disclosed in the Svedman U.S. Pat. No. 4,382,441; a product and process for establishing a sterile area of skin disclosed in the Groves U.S. Pat. No. 3,367,332; and the transdermal infusion device disclosed in the Westin U.S. Pat. No. 4,605,399. Equipment has also been available which flushes and collects contaminants from wounds.

Heretofore, there has not been available a patient interface system and method with the advantages and features of the present invention.

SUMMARY OF THE INVENTION

In the practice of the present invention, a patient interface system is provided which includes a fluid transfer subsystem with a primary transfer element and a secondary transfer element/manifold. An interface drape subsystem includes first and second drapes for covering the first and second fluid transfer elements respectively. A fluid conveyance subsystem includes a vacuum source connected to the secondary fluid transfer element/manifold by a suction tube and a fluid source connected to the primary fluid transfer element by a tubing system. In the practice of the method of the present invention, a method of interfacing fluid management equipment with a medical patient includes the steps of sizing and placing a primary fluid transfer element, draping the primary fluid transfer element with a primary drape, cutting an outlet opening in the primary drape, inserting a suction tube in a secondary fluid transfer element/manifold, placing the secondary fluid transfer element/manifold over the drape outlet opening; draping the secondary fluid transfer element/manifold; applying a sub-atmospheric, negative vacuum source to the primary transfer element via the suction tube and the secondary fluid transfer element/manifold; and connecting a fluid supply to the primary transfer element via an inlet tubing subassembly.

OBJECTS AND ADVANTAGES OF THE INVENTION

The principal objects and advantages of the present invention include: providing a patient interface system for interfacing a vacuum source with a patient wound site; providing such a system which interfaces a fluid source with a patient; providing such a system which can be used to uniformly distribute a vacuum force over a wound site; providing such a system which can minimize interference from clogging caused by matter in fluid being drained; providing such a system which is adapted to introduce fluids to a wound site; providing such a system which can reduce the frequency of dressing changes in connection with treating a wound; providing such a system which can provide for the effective control of various operating parameters in wound treatment with a hydrophobic foam rubber sponge material; providing such a system which is particularly designed for use with automated vacuum drainage equipment; providing such a system which can promote significantly faster healing; and providing such a system which is economical to manufacture, efficient in operation and particularly well-adapted for the proposed usage thereof.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 2 is a fragmentary perspective view of the patient interface system, particularly showing the application of a primary fluid transfer element and a primary drape thereof.

FIG. 3 is a perspective view of an assembled patient interface system embodying the present invention.

DETAILED DESCRIPTION OF THE PREFERRED EMBODIMENTS

Figure 1:
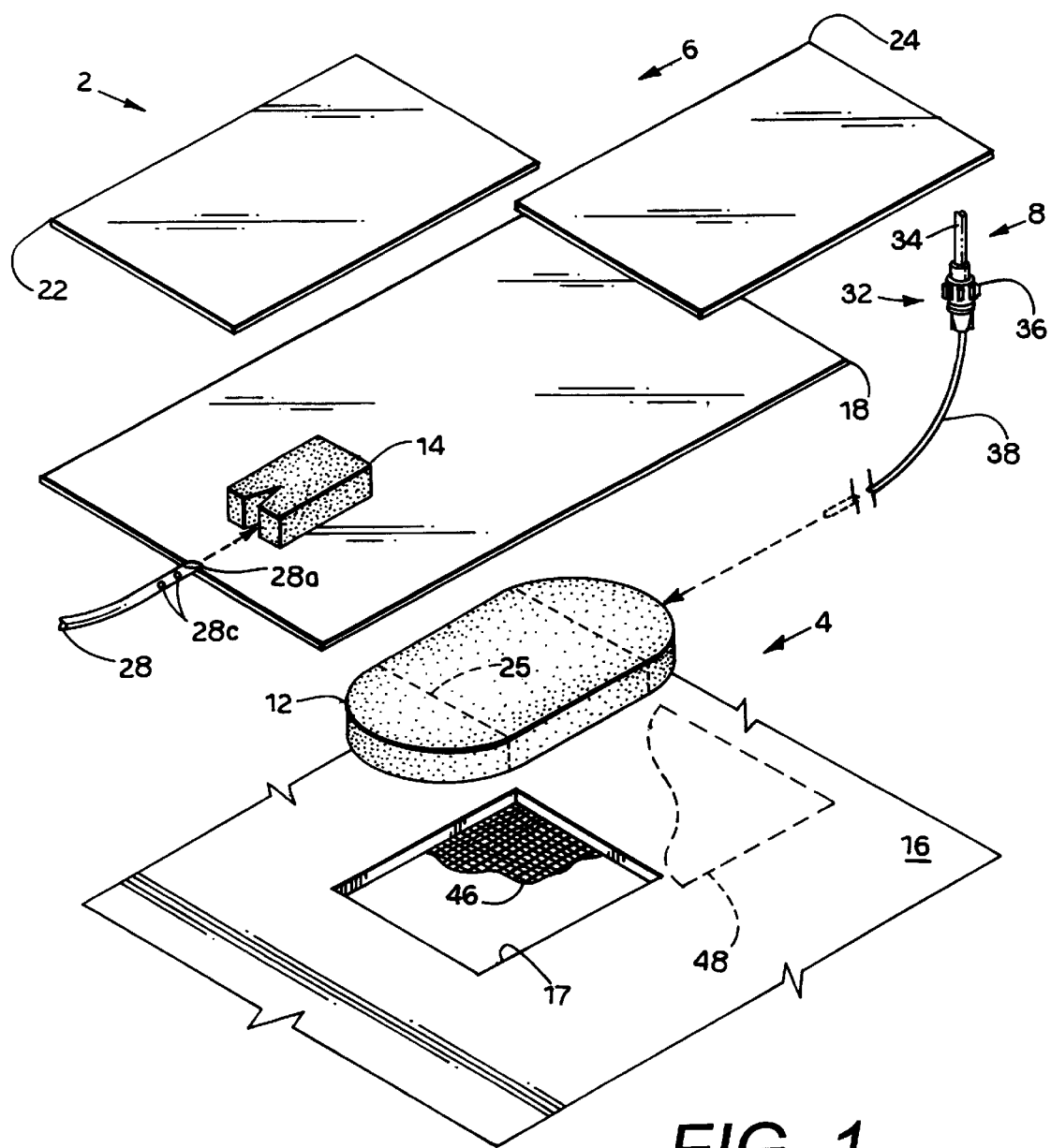
FIG. 1 is an exploded, perspective view of a patient interface system embodying the present invention.

I. Introduction and Environment.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring to the drawings in more detail, the reference numeral 2 generally designates a patient interface system embodying the present invention. The interface system 2 generally comprises a fluid transfer subsystem 4, an interface drape subsystem 6, and a fluid conveyance subsystem 8.

II. Fluid Transfer Subsystem 4.

The fluid transfer subsystem 4 includes a primary fluid transfer element 12 which can comprise, for example, a suitable open-cell, porous foam material (e.g., polyurethane ester). The degree of hydrophobic versus hydrophilic properties of the material comprising the element 12 can be determined by the particular application of the interface system 2. For wound drainage and for the introduction of various liquid medications and treatments, a large-cell, hydrophobic material is preferred. For example, hydrophobic polyurethane ether has been found to be a suitable material for many applications. Likewise, polyvinyl acetate (PVA) or small-cell, hydrophilic polyurethane foam can be used for its hydrophilic properties where such are desired. The primary fluid transfer element 12 includes a bottom or contact surface 12a, a top surface 12b, a perimeter 12c and an interior portion 12d of the top surface 12b.

Figure 4A:
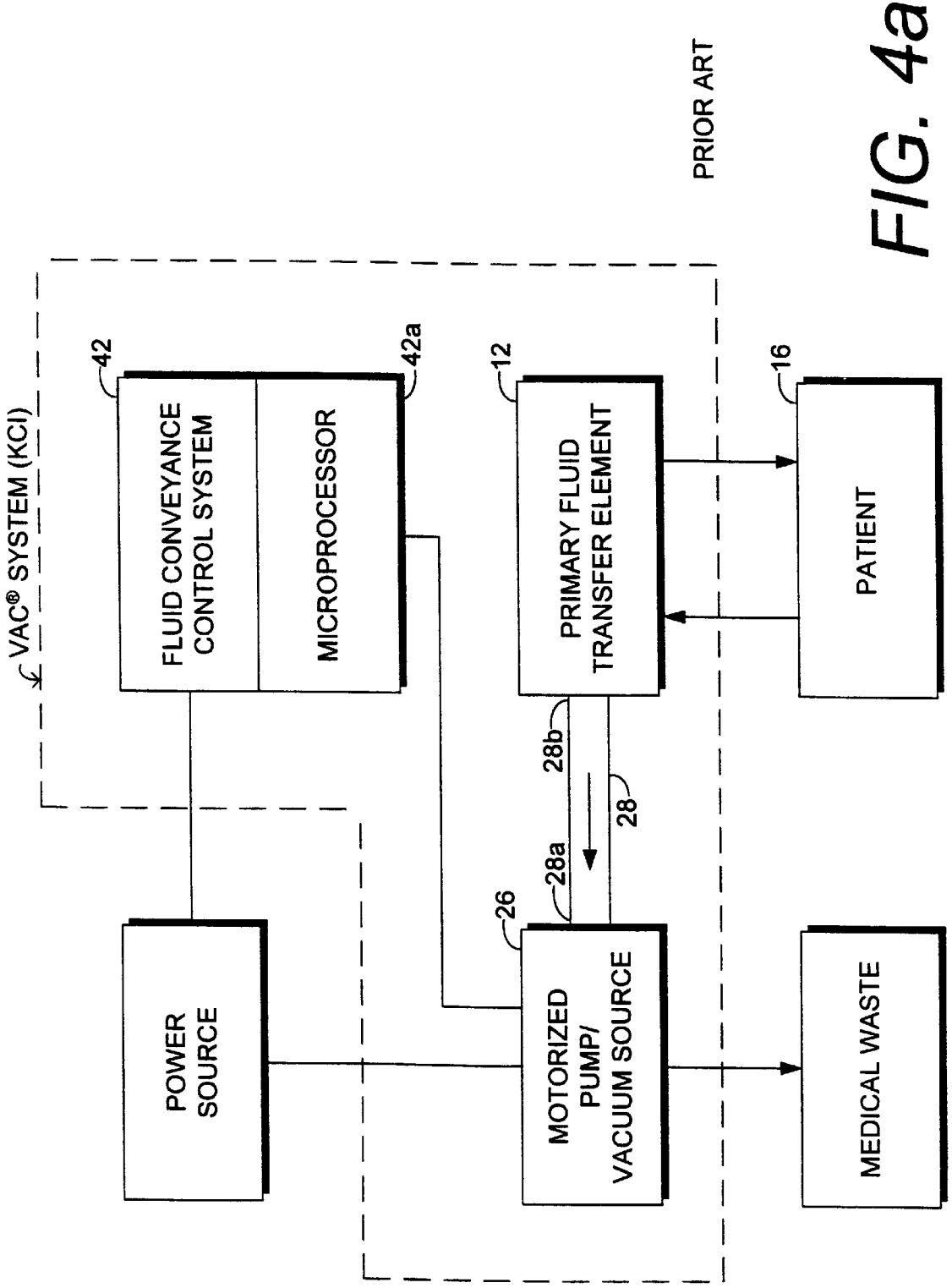
FIG. 4a is a schematic diagram of a prior art patient interface system.
Figure 4B:
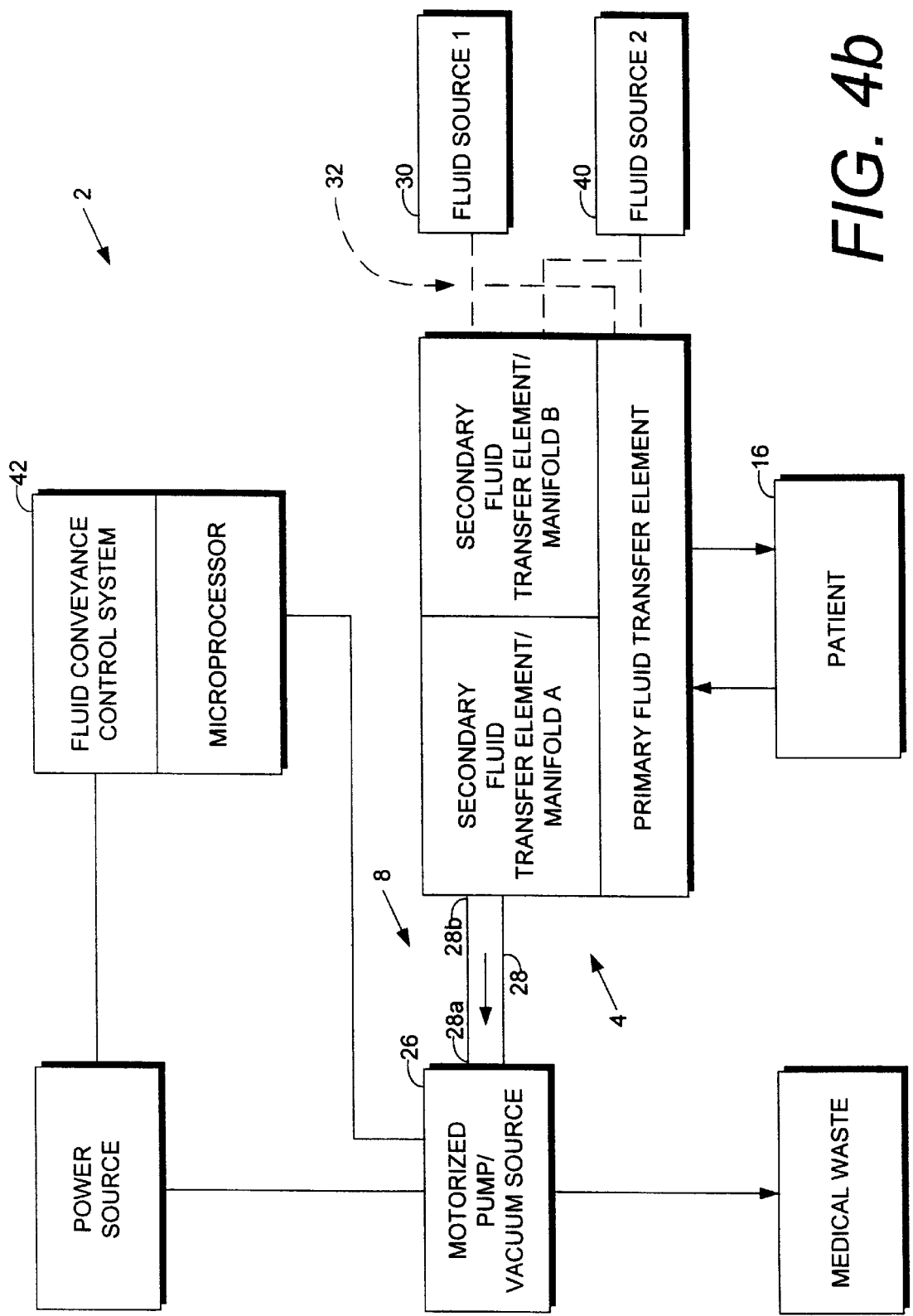
FIG. 4b is a schematic diagram of the patient interface system embodying the present invention.
Figure 5:
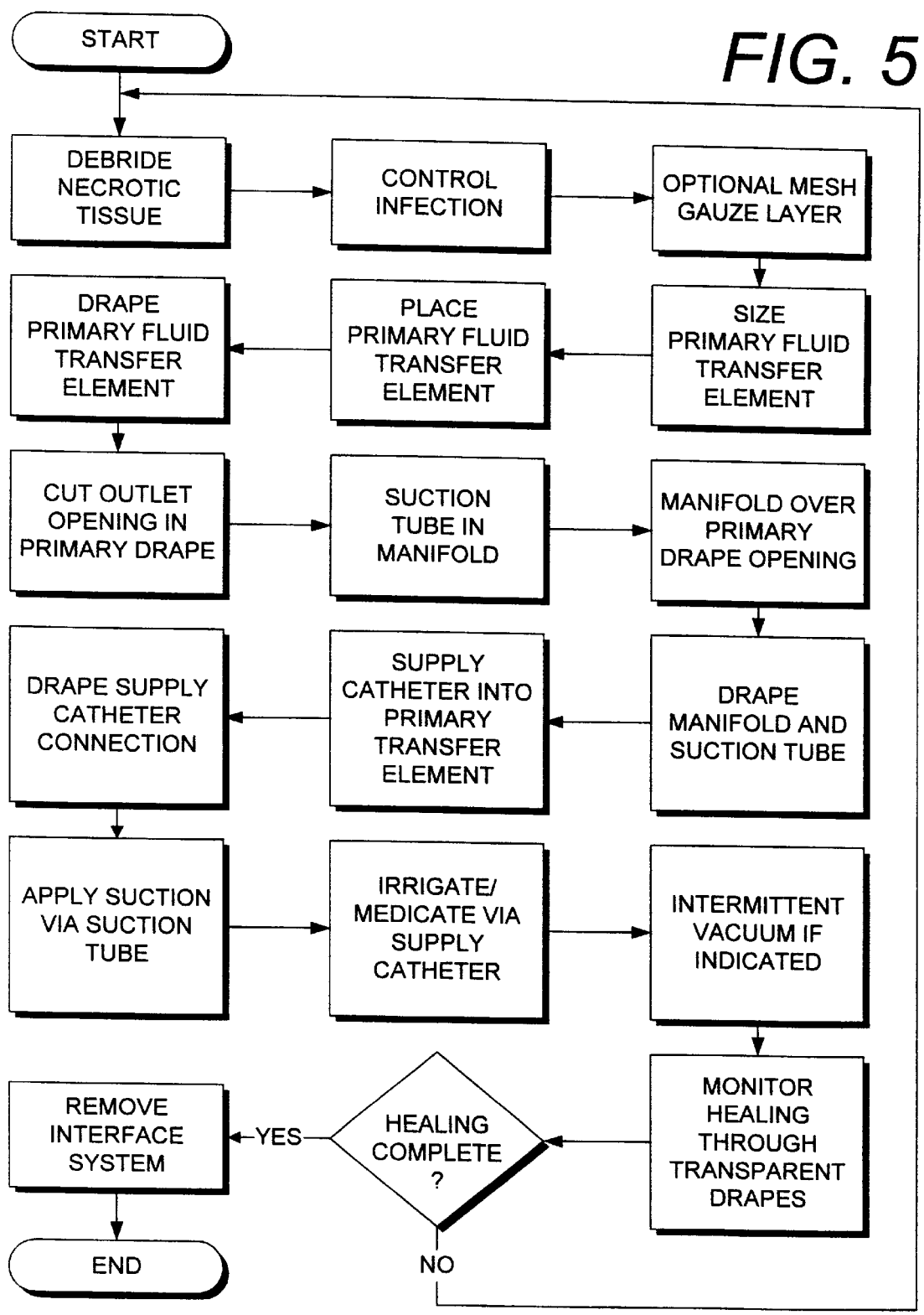
FIG. 5 is a flow chart showing the steps of the method of the present invention.

A secondary fluid transfer element/manifold 14 also preferably comprises a suitable foam material and includes a bottom or contact surface 14a, a top surface 14b, a perimeter 14c and an interior portion 14d. A pair of secondary fluid transfer elements/manifolds 14.1 and 14.2 can be provided for handling evacuation and supply respectively as shown in FIG. 4b, and each can be connected to the primarily fluid transfer element 12 in the manner described.

III. Interface Drape Subsystem 6.

An interface drape subsystem 6 is provided for draping or covering the fluid transfer subsystem 4 and the areas surrounding same on a patient 16. The drape subsystem 6 includes a primary drape 18 placed over the primary fluid transfer element 12 and extending beyond its perimeter 12c. The drape 18 can have one or more openings formed therein, such as the inlet and outlet openings shown at 20a,b for respectively admitting fluid to and extracting fluid from the primary transfer element 12. Additional drape subsystem components can include an inlet access drape 22 and an outlet access drape 24, the latter covering the secondary fluid transfer element/manifold 14 in the example shown.

The drapes 18, 22, 24 can comprise any suitable material, although a semi-permeable membrane is often preferred for facilitating wound healing by selectively admitting air while retaining liquids and minimizing the risk of infection by excluding contaminates. An example of such a material is marketed under the trademark "TEGADERM®" by the Minnesota Mining and Manufacturing Company (3M) of St. Paul, Minn. Other semi-permeable materials are available and can be successfully employed with the present invention. The drapes 18, 22, 24 preferably comprise a film material with a contact adhesive on one side thereof to facilitate adhering the drapes 18, 22, 24 to the patient 16 around a wound site 17, to the fluid transfer elements 12, 14 and to other components of the patient interface system 2. However, a non-adhesive material can be used for retention in place by vacuum pressure (i.e., negative, sub-atmospheric pressure) within the closed system in combination with positive atmospheric pressure acting externally on the closed interface system 2. Still further, one or more of the drapes 18, 22, 24 could be sized such that it could be wrapped around a patient and held in place by a suitable securing action. One or more of the drapes 18, 22, 24 could be applied as a single patch panel; as a face-to-face pair of opposing panels; or as a folded sheet and, furthermore, could comprise an impervious, impermeable material with suitable inlet and outlet openings, such as those shown at 22, 24, to admit and extract various combinations of fluids.

IV. Fluid Conveyance Subsystem 8.

The fluid conveyance subsystem 8 functions to extract fluids, including the patient's blood, serum, etc., from the interface system 2, and also to introduce various fluids, such as antibiotics, analgesics and growth factors into the interface system 2. A vacuum source 26 can comprise, for example, a vacuum assisted closure "VAC®R" system available from Kinetic Concepts, Inc. of San Antonio, Tex. The "VAC®" system provides a motorized pump, a fluid collection receptacle, variable pressure control, variable timing and automatic safety shut-down features in a single, portable unit which can be pre-programmed to apply suction either intermittently for a pulsatile effect with predetermined frequency, amplitude and duration of the sub-atmospheric pressure gradient or continuously in a constant pressure mode of operation.

A suction tube 28 includes a proximate end 28a embedded in the secondary fluid transfer element/manifold 14 and a distal end 28b connected to the vacuum source 26. The suction tube proximate end 28a can be provided with multiple orifices 28c to facilitate distribution of the suction force throughout the secondary transfer element/manifold 14.

A primary fluid source 30 can comprise, for example, a suitable container and can be connected to the primary fluid transfer element 12 by an inlet tubing subassembly 32 which can comprise, for example, the type commonly used for intravenous applications with tubing 34, suitable leur lock connectors 36 and a catheter 38 for interfacing same with the primary fluid transfer element 12. A secondary fluid source 40 can supplement the primary fluid source 30 to achieve a desired flow of fluid, medication, growth factor, etc. into the patient interface system 2.

A fluid conveyance control system 42 includes a suitable microprocessor 42a and is connected to the vacuum source 26. The controller 42 controls pressures, flow rates, timing sequences of intermittent vacuum, and includes control features which permit the shut-down of the system 2 or its automated use. The controller 42 can comprise, for example, the control features in a VAC® vacuum-assisted closure system and its on-board computer can comprise the controller microprocessor 42a.

The connections of the suction tube 28 and the inlet tubing subassembly 32 with the primary and secondary fluid transfer elements 12, 14 can be suitably covered by the inlet and outlet access drapes 22, 24. Moreover, the secondary fluid transfer element/manifold 14 is preferably placed over the outlet opening 20b formed in the primary drape 18. With the addition of the secondary drapes 22, 24, the fluid conveyance subsystem 8 is fluidically connected to the fluid transfer subsystem 4.

V. Operation.

The patient interface system 2 is adaptable for use in connection with various medical procedures responsive to particular patient conditions. For example, wound drainage can be accomplished by applying the primary fluid transfer element 12, which can be cut (e.g., at cut lines 25) to an appropriate size and configuration for a particular wound, covering it with a primary drape 18 and forming an outlet opening 20b therein. A secondary fluid transfer element 14 functions as a manifold for communicating negative vacuum pressure to the primary fluid transfer element 12 and is placed over the drape outlet opening 20b with an outlet access drape 24 thereover. The outlet access drape 24 functions to retain the secondary fluid transfer element/manifold 14 in its proper position on top of the primary transfer element 12, and also facilitates directing fluids from the wound to the suction tube 28. The controller 42 can be programmed to provide either continuous or intermittent suction via the vacuum source 26 at suitable predetermined intervals and pressures. Multiple pressure settings can be utilized, if necessary.

The hydrophobic, porous characteristics of the transfer elements 12, 14 facilitate efficient passage of patient fluids therethrough, including various matter such as serum, protein, blood, etc. Moreover, creating sub-atmospheric pressure (i.e., negative pressure) within the closed environment of the interface system 2 can help control edema in the wound area and in the surrounding tissues. The edema-countering effects of the interface system 2 can be varied by setting the controller 42 at different appropriate pressure settings and timing sequences.

Liquid supply operations are accomplished by inserting the catheter 38 into the primary transfer element 12. The connection can then be covered with an inlet access drape 22. Various other fluid-type connections can be utilized for introducing fluid (e.g., air, nitrogen, oxygen, etc.) into the system 2. For example, an additional secondary transfer element 14 for fluid supply purposes could be formed of a similar, porous, hydrophobic material. The porous, hydrophobic characteristics of the primary transfer element 12 facilitate distribution of fluids introduced into the interface system 2 over the entire wound area. Moreover, by controlling the vacuum sub-atmospheric pressures and timing, the fluids introduced can be allowed to accumulate on the wound for absorption into the patient's system. Thus, antibiotics and anesthetics can be effectively delivered for maximum benefit. The wound can also be effectively flushed since the transfer elements 12, 14 act as efficient conduits of liquids with continuous flow therethrough under operating conditions. The system 2 effectively differentiates gases and liquids in a controlled environment for optimizing therapeutic benefits. Other fluid supply corrections include an injection port 33 connected to the tubing 34 and a vent 35 connected to the primary fluid transfer element 12.

The interface system 2 can be used for skin graft donor sites, which are often initially covered with a material such as rayon gauze material 46. The drape 18 can comprise a material such as TEGADERM® which is a vapor-permeable polyurethane film. Thrombin can be introduced to the donor site. Drying of the donor site can be controlled by the controller 42 operating the vacuum source 26, and also by introduction of other fluids. By way of example, sub-atmospheric (vacuum) pressure in the range of approximately 75–125 millimeters of vacuum force on continuous operating mode for three days has been found to promote effective skin graft donor site exudate control to a point at which the donor site can be covered by a highly permeable material, such as "OPSITE 3000®" material. Such a highly permeable material can maintain continued drying of the wound site 17 to promote epithelial maturation without the application of additional sub-atmospheric (vacuum) pressure and with little or no need for additional dressing changes. The rayon and the drape materials are both relatively transparent and thus permit observation of the peri-wound area for monitoring the patient's condition.

By way of example, the following steps would be involved in the treatment of a skin graft donor site utilizing the interface system and method of the present invention:

1. Apply rayon 46 to the donor bed, with the optional topical application of banked, unused skin graft therebelow and the optional application of thrombin.
2. Application of the primary fluid transfer element 12 directly on top of and just overlapping the rayon 46.
3. Application of the primary drape 18 over the primary fluid transfer element 12, with the drape 18 adhesively secured to the patients' surrounding, healthy skin.
4. Form a suitable outlet drape opening 20b and secure the secondary fluid transfer element/manifold 14 (connected to the suction tube 28) over the drape outlet opening 20b. The outlet access drape 24 is then placed in covering relation over the secondary transfer element/manifold 14, the suction tube 28 where it enters same and a portion of the primary drape 18 around the outlet opening 20b.
5. Continuous suction by the vacuum source 26 at 75–125 millimeters vacuum for approximately 72 hours.
6. Through a separate delivery site, either a catheter with a sealing injection port fixed by placing a drape patch thereover, or by an injection with a needle and a drape film adhesive patch sealing the injection site, liquid fluids can be instilled. For example, saline can be instilled to flush blood film. Growth factors and/or antibiotics can be added. Just before a dressing change, Xylocaine® local anesthetic can be instilled to control pain and can be effectively, quickly and uniformly disbursed due to the hydrophobic nature of the primary fluid transfer element 12.
7. Removal of the primary drape 18 and the primary fluid transfer element 12 to expose the rayon dressing 46.

8. Application of a highly permeable polyurethane film layer 48 (e.g., OPSITE® 3000) in covering relation over the rayon dressing 46.

9. Monitor donor site for drying as a sign of reepithelialization and maturation for about 2–3 weeks, whereupon spontaneous separation of the rayon dressing 46 or "OPSITE 3000®" film occurs.

Another application of the interface system 2 is for low-pressure (e.g., about 50 millimeters vacuum) for a predetermined time period of, for example, about one hour while liquid is introduced through the fluid source 40. The lower pressure allows the liquid to remain in the interface system 2 longer than it would at a higher vacuum pressure.

VI. First Modified Embodiment Patient Interface System 102.

Figure 6:
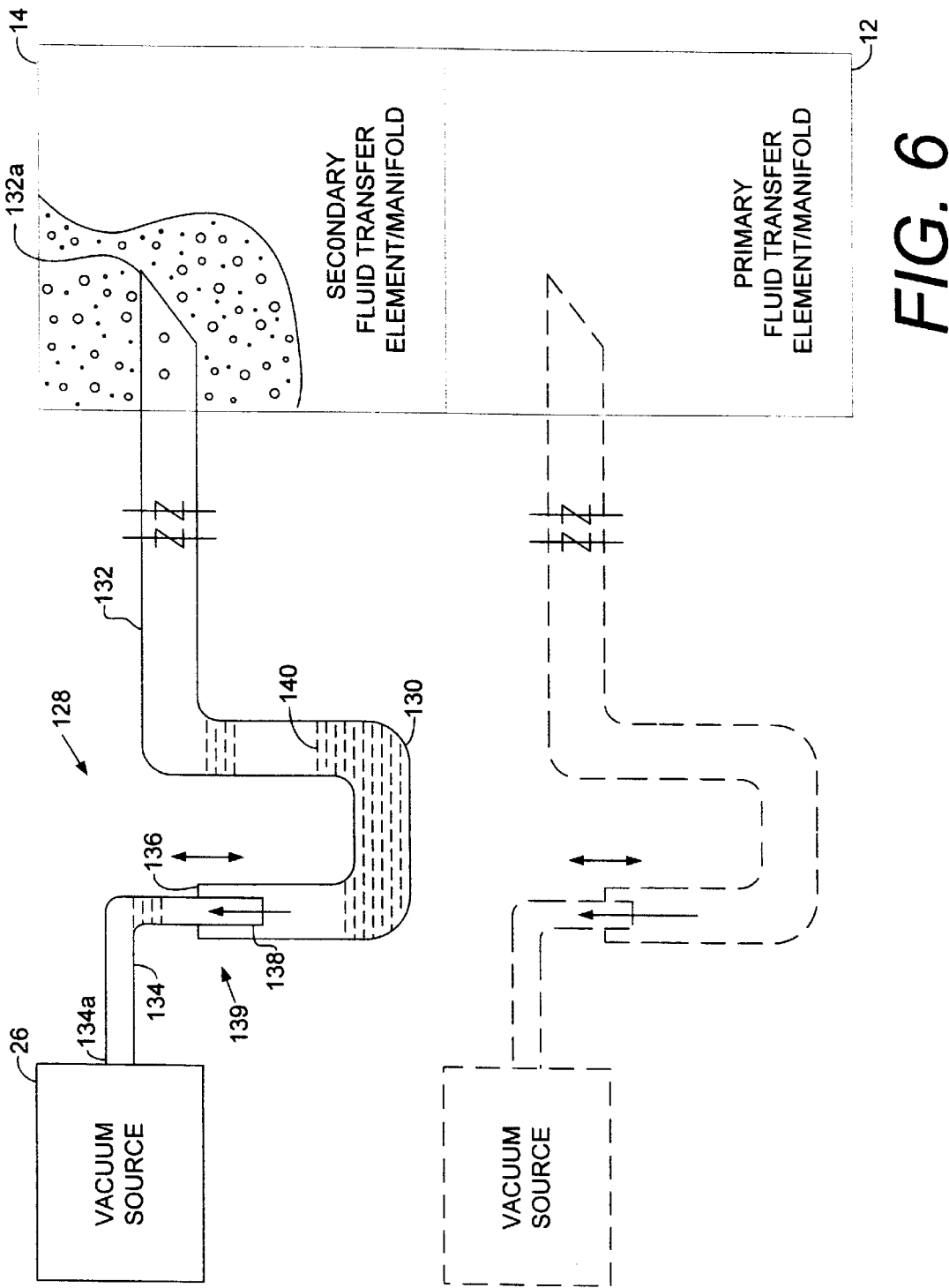
FIG. 6 is a schematic diagram of a patient interface system comprising a first modified embodiment of the present invention.

FIG. 6 shows a patient interface system 102 comprising a first modified embodiment of the present invention. The patient interface system 2 includes a modified fluid conveyance subsystem 108 with a suction tube 128 forming an adjustable drop P-trap 130. The P-trap 130 includes a proximate section 132 with a proximate end 132a connected to either the primary fluid transfer element 12 or the secondary fluid transfer element/manifold 14 and a P-trap distal section 134 having a distal end 134a connected to the vacuum source 26. A female telescoping portion 136 telescopically and vertically-adjustably receives a mail telescoping portion 138 of the P-trap distal section 134.

A fluid seal 140 is formed in the P-trap 130. The depth of the fluid seal 140 is controlled by a telescopic interconnection 139 of the P-trap sections 132, 134. Thus, the deeper the P-trap 130, the greater the pressure gradient across the suction tube 128 required to draw gas through the suction tube 128. Under certain conditions of wound drainage, vacuum, fluid seal 140 and P-trap 130 depth, gas bubbles intermittently pass through the suction tube 128 and create a pulsatile effect in the patient interface system 102. The amplitude, frequency and duration of the pressure waves representing the pulse can be controlled by varying the different operating parameters, including the depth of the P-trap 130 and the sub-atmospheric vacuum force drawn by the vacuum source 26. A pulsatile effect approximately the pulse of the patient 16 can be achieved. Such a pulsatile effect can have benefits in the treatment of certain wounds, including the stimulation of cell growth and the stimulation of circulation to the wound area 17.

VII. Second Modified Embodiment Patient Interface System 202.

Figure 7:
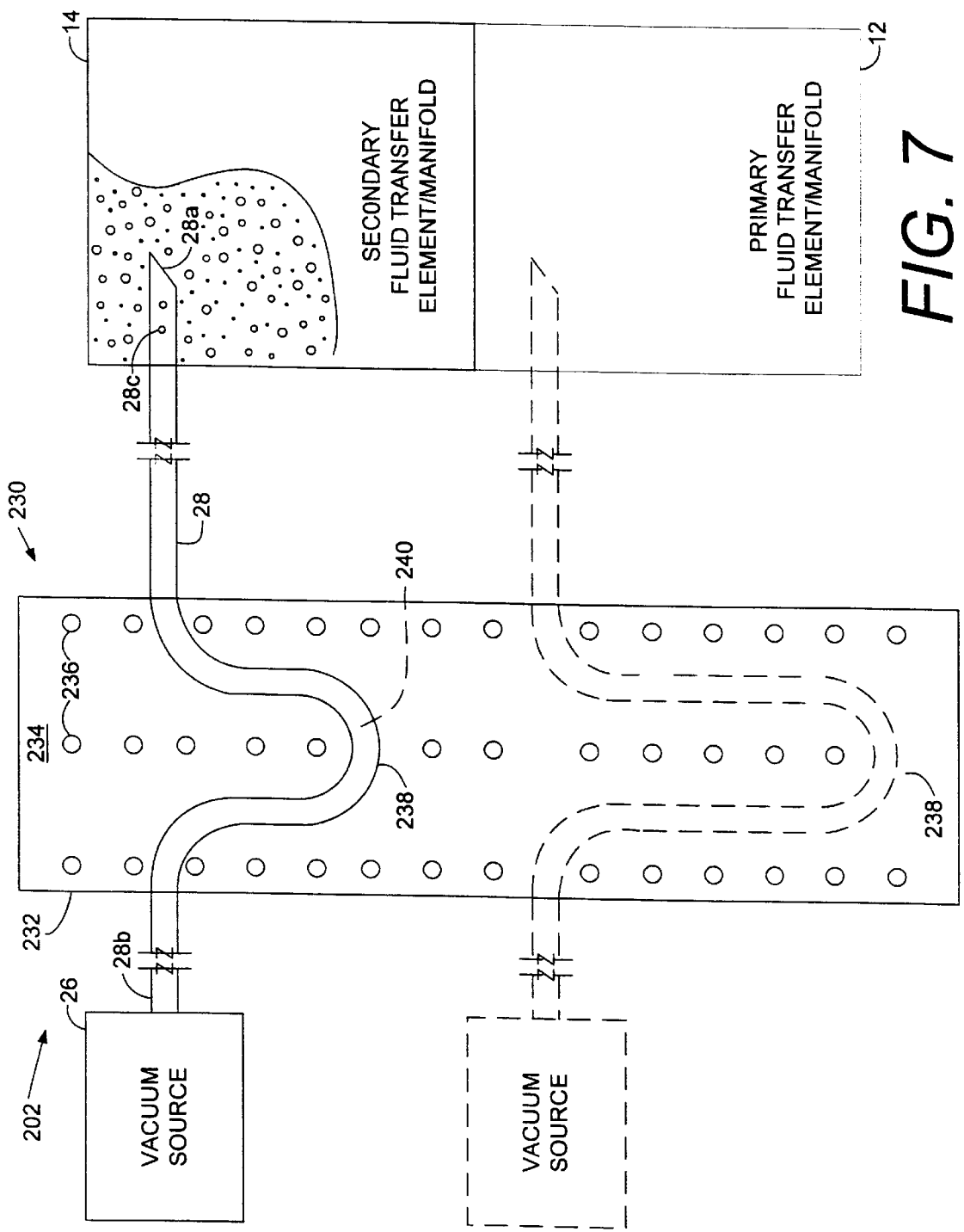
FIG. 7 is a schematic diagram of a patient interface system comprising a second modified embodiment of the present invention.

FIG. 7 is a schematic diagram of a patient interface system 202 with a further modified P-trap subassembly 230 including a tube shaper 232 comprising a back panel 234 and an array of pins 236 projecting outwardly therefrom. The pins 236 are arranged in an array comprising three columns with each column containing a number of rows. Different numbers and arrangements of pin arrays could also be employed. Different tube shaper configurations could also be used. For example, various types of pins, knobs, clips, etc. can be used for forming the downwardly-depending loops, such as that shown at 238, in the flexible tubing 32. As with the first modified embodiment patient interface system 102, a liquid seal 240 is formed by the loops 238, and its resistance to the passage of gas through the exhaust tube 32 is determined by the depth of the loop 238, the viscosity of the liquid therein, the pressure gradient across the P-trap subassembly 230, etc. The P-trap subassembly 230 can be formed with the flexible suction tube 28, which can thus be continuous between either the primary or the secondary transfer elements 12, 14 and the vacuum source 26.

It is to be understood that while certain forms of the present invention have been illustrated and described herein, it is not to be limited to the specific forms or arrangement of parts described and shown.

What is claimed and desired to be secured by Letters Patent is as follows:

1. A patient fluid management interface system, which comprises:
   (a) a primary fluid transfer element including a patient contact surface, a plurality of passages communicating with said contact surface, an outer surface and a perimeter;
   (b) a film material drape placed over said primary fluid transfer element in contact with the outer surface thereof and adapted for contact with the patient around the perimeter of said primary fluid transfer element;
   (c) vacuum force communicating means for distributing a sub-atmospheric, negative vacuum force through said primary fluid transfer element to said patient contact surface thereof;
   (d) fluid differentiating means for drawing gas into said interface system and containing and directing liquid within said interface system;
   (e) a vacuum source; and
   (f) a vacuum tube with a proximate end connected to the primary fluid transfer element and a distal end connected to said vacuum source.

2. The interface system according to claim 1, which includes:
   (a) said primary fluid transfer element comprising an open-cell foam material.

3. The interface system according to claim 2 wherein said primary fluid transfer element comprises hydrophobic polyurethane ether.

4. The interface system according to claim 1, which includes:
   (a) said primary fluid transfer element having a first, larger size and configuration under ambient atmospheric pressure and a second, smaller, compressed size and configuration under sub-atmospheric pressure.

5. The interface system according to claim 1 wherein:
   (a) said drape includes an inner, adhesive contact layer.

6. The interface system according to claim 1, which includes:
   (a) said drape being applied non-adhesively to said patient.

7. The interface system according to claim 6, which includes:
   (a) said drape being retained on said patient by a pressure gradient across said drape formed by a sub-atmospheric pressure within said interface system and an ambient, atmospheric pressure external to said interface system.

8. The interface system according to claim 6, which includes:
   (a) said drape being wrapped around a portion of the patient.

9. The interface system according to claim 1, which includes:
   (a) a P-trap formed in said vacuum tube.

10. The interface system according to claim 9, which includes:
    (a) said suction tube including a proximate section with an end located adjacent to said P-trap and a distal section with an end located adjacent to said P-trap; and
    (b) said vacuum tube ends being telescopically, adjustably interconnected.

11. The interface system according to claim 9, which includes:
(a) a tube shaper including a plurality of tube engagement means, each said tube engagement means being adapted to retain a portion of the tube at a predetermined location to form said P-trap.

12. A patient fluid management interface system, which comprises:
(a) a primary fluid transfer element including a patient contact surface, a plurality of passages communicating with said contact surface, an outer surface and a perimeter;
(b) a film material drape placed over said primary fluid transfer element in contact with the outer surface thereof and adapted for contact with the patient around the perimeter of said primary fluid transfer element;
(c) vacuum force communicating means for distributing a sub-atmospheric, negative vacuum force through said primary fluid transfer element to said patient contact surface thereof;
(d) fluid differentiating means for drawing gas into said interface system and containing and directing liquid within said interface system;
(e) a vacuum source;
(f) a vacuum tube with a proximate end connected to the primary fluid transfer element and a distal end connected to said vacuum source;
(g) said force communicating means comprising a secondary fluid transfer element including a contact surface, a plurality of passages communicating with said contact surface and an outer surface; and
(h) mounting means for mounting said secondary fluid transfer element on said primary fluid transfer element.

13. The interface system according to claim 12, which includes:
(a) said vacuum tube intersecting said secondary fluid transfer element at the outer surface thereof;
(b) said drape comprising a first drape; and
(c) a second film material drape placed over said secondary fluid transfer element and said intersection of said tube therewith.

14. The interface system according to claim 12, which includes:
(a) said secondary fluid transfer element comprising an open-cell foam material.

15. The interface system according to claim 14 wherein said secondary fluid transfer element comprises hydrophobic polyurethane ether.

16. A patient fluid management interface system, which comprises:
(a) a primary fluid transfer element including a patient contact surface, a plurality of passages communicating with said contact surface, an outer surface and a perimeter;
(b) a film material drape placed over said primary fluid transfer element in contact with the outer surface thereof and adapted for contact with the patient around the perimeter of said primary fluid transfer element;
(c) vacuum force communicating means for distributing a sub-atmospheric, negative vacuum force through said primary fluid transfer element to said patient contact surface thereof;
(d) fluid differentiating means for drawing gas into said interface system and containing and directing liquid within said interface system;
(e) a vacuum source;
(f) a vacuum tube with a proximate end connected to the primary fluid transfer element and a distal end connected to said vacuum source;
(g) a fluid source;
(h) fluid source tubing with a proximate end connected to said first fluid transfer element and a distal end connected to said fluid source;
(i) said fluid source comprising a first fluid source connected to said fluid source tubing; and
(j) a second fluid source connected to said fluid source tubing.

17. The interface system according to claim 16, which includes:
(a) said fluid source tubing mounting a catheter on its proximate end for insertion in said fluid transfer element.

18. A patient fluid management interface system, which comprises:
(a) a primary fluid transfer element including a patient contact surface, a plurality of passages communicating with said contact surface, an outer surface and a perimeter;
(b) a film material drape placed over said primary fluid transfer element in contact with the outer surface thereof and adapted for contact with the patient around the perimeter of said primary fluid transfer element;
(c) vacuum force communicating means for distributing a sub-atmospheric, negative vacuum force through said primary fluid transfer element to said patient contact surface thereof;
(d) fluid differentiating means for drawing gas into said interface system and containing and directing liquid within said interface system;
(e) a vacuum source;
(f) a vacuum tube with a proximate end connected to the primary fluid transfer element and a distal end connected to said vacuum source;
(g) a fluid source;
(h) fluid source tubing with a proximate end connected to said first fluid transfer element and a distal end connected to said fluid source; and
(i) an injection port mounted on and selectively fluidically connected to said fluid source tubing.

19. A patient fluid management interface system, which comprises:
(a) a primary fluid transfer element including a patient contact surface, a plurality of passages communicating with said contact surface, an outer surface and a perimeter;
(b) a film material drape placed over said primary fluid transfer element in contact with the outer surface thereof and adapted for contact with the patient around the perimeter of said primary fluid transfer element;
(c) vacuum force communicating means for distributing a sub-atmospheric, negative vacuum force through said primary fluid transfer element to said patient contact surface thereof;
(d) fluid differentiating means for drawing gas into said interface system and containing and directing liquid within said interface system;
(e) a vacuum source;
(f) a vacuum tube with a proximate end connected to the primary fluid transfer element and a distal end connected to said vacuum source;

(g) a fluid source;

(h) fluid source tubing with a proximate end connected to said first fluid transfer element and a distal end connected to said fluid source;

(i) said fluid source comprising the atmosphere; and (j) a vent connected to the fluid source tubing distal end for selectively communicating the atmosphere with the fluid source tubing.

20. A patient fluid management interface system, which comprises:

(a) a primary fluid transfer element including a patient contact surface, a plurality of passages communicating with said contact surface, an outer surface and a perimeter;

(b) a film material drape placed over said primary fluid transfer element in contact with the outer surface thereof and adapted for contact with the patient around the perimeter of said primary fluid transfer element;

(c) vacuum force communicating means for distributing a sub-atmospheric, negative vacuum force through said primary fluid transfer element to said patient contact surface thereof;

(d) fluid differentiating means for drawing gas into said interface system and containing and directing liquid within said interface system;

(e) a vacuum source;

(f) a vacuum tube with a proximate end connected to the primary fluid transfer element and a distal end connected to said vacuum source;

(g) a fluid source;

(h) fluid source tubing with a proximate end connected to said first fluid transfer element and a distal end connected to said fluid source; and (i) an inlet access film material drape placed over said interconnection of said fluid source tubing proximate end and said first fluid transfer element.

21. A patient fluid management interface system, which comprises:

(a) a primary fluid transfer element including a patient contact surface, a plurality of passages communicating with said contact surface, an outer surface and a perimeter;

(b) a film material drape placed over said primary fluid transfer element in contact with the outer surface thereof and adapted for contact with the patient around the perimeter of said primary fluid transfer element;

(c) vacuum force communicating means for distributing a sub-atmospheric, negative vacuum force through said primary fluid transfer element to said patient contact surface thereof;

(d) fluid differentiating means for drawing gas into said interface system and containing and directing liquid within said interface system;

(e) a vacuum source;

(f) a vacuum tube with a proximate end connected to the primary fluid transfer element and a distal end connected to said vacuum source;

(g) a P-trap formed in said vacuum tube; and (h) a tube shaper including a plurality of tube engagement means, each said tube engagement means being adapted to retain a portion of the tube at a predetermined location to form said P-trap.

22. The interface system according to claim 21 wherein said tube shaper includes a back panel and said tube engagement means comprises a plurality of pins projecting from said back panel, said pins being arranged in multiple rows and columns.

* * * * *